United States Patent [19]

Sullivan

[11] Patent Number: 5,087,197
[45] Date of Patent: Feb. 11, 1992

[54] DISC AND SLEEVE ASSEMBLY FOR COUPLING DIE SEGMENTS OF A DENTAL MODEL TO A BASE

[75] Inventor: Jerry F. Sullivan, Ridgewood, N.J.
[73] Assignee: Coltene/Whaledent, New York, N.Y.
[21] Appl. No.: 306,949
[22] Filed: Feb. 6, 1989
[51] Int. Cl.⁵ ............................................. A61C 19/00
[52] U.S. Cl. ..................................................... 433/74
[58] Field of Search ..................... 433/74, 53, 213, 60

[56]   References Cited
U.S. PATENT DOCUMENTS

| | | | |
|---|---|---|---|
| 2,851,728 | 9/1958 | Spalten et al. | 433/74 |
| 4,054,995 | 10/1977 | Yoshida | 433/74 |
| 4,205,443 | 6/1980 | Weissman | 433/74 |

*Primary Examiner*—Cary E. Stone
*Attorney, Agent, or Firm*—Helfgott & Karas

[57] ABSTRACT

A dental disc and sleeve assembly for removably coupling die portions of teeth from a dental model onto a cast base. The disc is inserted into a semi-circular cut formed in the underside of the die portions so that the disc is secured in the die and partially protrudes therefrom. A sleeve secured in the cast base has a head portion having a chamber matingly receiving the protruding portion of the disc and a tail portion. Two knobs provided on the opposite sides of the disc are snapped into two grooves formed at two opposite sides of the chamber. The grooves can release the knobs and the disc can be removed from the sleeve when slight pressure is applied to the tail portion of the sleeve to remove the die portion from the cast base.

44 Claims, 4 Drawing Sheets

DISC AND SLEEVE ASSEMBLY FOR COUPLING DIE SEGMENTS OF A DENTAL MODEL TO A BASE

BACKGROUND OF THE INVENTION

The present invention relates to models utilized in restorative dentistry in general, and more particularly to an improvement in arrangements which permit coupling and separation as well as replacement of a denial die on a cast base.

It has been well known in restorative dentistry to form an impression of a dentition to be restored and then reproduce such dentition in the form of a dental model made from plaster, artificial stone or the like. After the dental model has been accurately formed it is necessary to cut the dental model into sections which represent one or more teeth needing correction or to be used for the formation of a prosthesis. The problem, however, is that the segments or dies must be often removed and replaced from its cast base without disturbing adjacent segments or damaging its own form. Also, the die should be indexed in the model to be repositioned with great accuracy after removal. Various means for removably coupling such model segments or dies to the cast base have been proposed. Typically, various pin systems have been employed, which utilize pins fixed in a die and projecting outwardly therefrom. Such pins are received in holes provided for this purpose in the cast base.

Dowel pins are frequently employed for coupling the dies to the cast base. These pins are initially positioned over an impression tray and maintained suspended over the tray. The material of the model is then poured into the impression tray to form the dental model or full cast of the prepared teeth to be worked on. While the plaster, or other comparable material, is in a soft state this material will fully surround the pins to embed the same in the model. After the model has hardened the stems of the dowel pins will project outwardly from the model. After the model has fully hardened with the pins projecting therefrom, a separator medium, such as "Vaseline" is placed on the lower surface of the model. Thereupon, additional stone or plaster material is poured on or applied to the lower wall of the model to form a cast base. The cast base and the model are fully hardened and cured. As a result, holes are formed in the cast base at the locations of the stems of the dowel pins. These holes conform to the contours of the pins. The model is then cut by a saw into segments or dies as described herein above. The dies with the pins can then be separated and removed from the cast base to be worked on and reinserted into the base. When the die is replaced into the base the pins are aligned in the corresponding receiving holes.

Prior to pouring the base, sleeves may be placed over the projecting pins and the sleeves are then cast into the base. The segments with the projecting pins can then be inserted and removed from the sleeves.

The PINDEX® System by the Whaledent Company has been, for example, developed for the orientation of the placement of removable dies into the cast. Such system is disclosed in U.S. Pat. No. 3,704,519. In the system of this patent, holes are provided in the removable part of the model. Pins with sleeves or bushings on them are inserted and pressed into the dental model. The stone is then poured on to the bushings as sleeves and the bushings or sleeves are cast into the base. The dies may be removed by pulling the pins from the bushings. At least two pins are necessary, for each die to ensure proper orientation and replacement of the die segments into the cast.

While the PINDEX® system has been widely accepted and used, it would appear to be desirable to have a system which would require only a single insertion and yet achieve the benefits of the PINDEX® system.

SUMMARY OF THE INVENTION

It is therefore an object of the present invention to provide a dental disc and sleeve assembly for providing a removable coupling of a die portion of a dental model into a cast base.

Another object of the invention is to provide a dental disc and sleeve assembly which ensures a proper orientation of a removable die section of a dental model into a cast base.

Still another object of the invention is to provide a dental disc and sleeve assembly which facilitates insertion and removal of a die section from a cast base.

Briefly, in accordance with the present invention, there is provided a dental disc and sleeve assembly for removably-coupling a die section of a dental model into a cast base. The assembly comprises an internal member including a first portion having a substantially circular shape and adapted for securement within the die, and a second portion protruding from the die to depend therefrom. The assembly also includes an external member including an elongated tail portion for securement within the cast base and a sleeve-shaped head portion receiving the protruding portion when the die is coupled into the cast base. The protruding portion of the internal member and the head portion of the external member includes cooperating lock means to guide the protruding portion upon insertion thereof into the external member and also provides a releasable snap-fit lock of the protruding portion into the head portion.

In an embodiment of the invention, the protruding portion has a semi-circular shape and in conjunction with the first portion of the internal member constitutes a complete disc.

In an embodiment of the invention, the head portion of the external member has a chamber shaped for matingly receiving the protruding portion of the disc.

In an embodiment of the invention, the lock means includes two knobs formed at opposing sides of the disc and correspondingly two grooves provided in the chamber of the head portion for receiving the knobs upon insertion of the protruding portion of the disc into the head portion.

In an embodiment of the invention, the head portion includes a hollow frame defining the chamber therein with the grooves forming recesses in opposing interior frame walls.

In an embodiment, the head portion of the external member is formed with outwardly protruding lugs positioned at two opposite ends thereof to retain the external member secured within the cast material of the base.

Grooves may be formed at the opposing sides of the disc. Those grooves would then receive knobs projecting from opposite walls of the head portion into the disc-receiving chamber of the head portion.

In accordance with the invention there is also provided a method of making a dental model wherein die segments of the model may be removed and remounted on a cast base, the method comprising sawing a plurality of substantially semi-circular cuts into a lower surface of the dental model opposite to that formed with the teeth, fixing a plug in each cut, each plug having a semi-cylindrical part which fits into the cut and a portion of the plug which projects normal to and outwardly from said lower surface of the model. The method further includes mounting sleeves onto the projecting portion of each plug. Each sleeve has a recess shaped to matingly receive said projecting portion of the plug. Cast material is then poured onto the lower surface of the model and onto the sleeves to thereby form the base. After the material hardens, the sleeves are secured. The model together with the plugs is removed from the hardened base, and the model is cut into die portions so that each die portion includes at least one plug with its projecting portion therefrom. The die portions are remountable on the base by insertion of the projecting portion of each plug into the recess of its respective sleeve.

The aforementioned objects, features and advantages of the invention will, in part, be pointed out with particularity, and will, in part, become obvious from the following more detailed description of the invention, taken in conjunction with the accompanying drawing, which form an integral part thereof.

BRIEF DESCRIPTION OF THE DRAWINGS

In the drawing:

FIGS. 9A to 12E show various modifications of the discs;

DETAILED DESCRIPTION OF THE PREFERRED EMBODIMENTS

Figure 1:
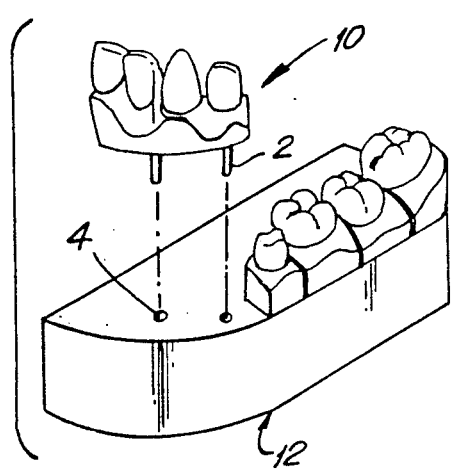
FIG. 1 is an exploded perspective view of the cast base and a die segment with two dowel pins protruding therefrom, according to the prior art.

Referring now to the drawings in detail, FIG. 1 illustrates a commonly used dowel pin system, in which two parallel pins 2 extending from the lower surface of a die segment 10 of a dental model are received in two corresponding holes 4 formed in the model base 12. In the PINDEX ® round parallel sided pins would be used and plastic sleeves would be cast in the model base 12 to receive the pins. Typically, one short pin and one long pin would be used.

Figure 2:
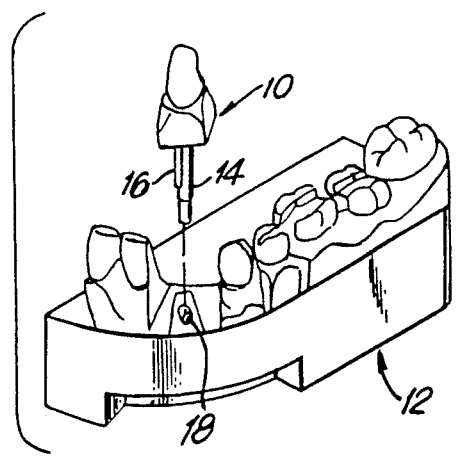
FIG. 2 is an exploded perspective view of the cast base with a pin receiving sleeve inserted in a hole formed in the cast base and a removable die with a pin therein, according to another system of the prior art.

FIG. 2 illustrates a post and sleeve system as is described in copending application Ser. No. 076,640 filed and assigned to the assignee of the present invention, which is a form of the PINDEX ® system. In this case an elongated substantially cylindrical body portion of a pin 14 has two diametrically opposing radially projecting ribs 16 extending along the length of the body portion 14 tangentially thereto. The pin 14 is received in a sleeve or bushing 18 which is then cast into the base 12. The sleeve has a bore of a shape corresponding to the body portion of the pin 14 so that the pin 14 snugly fits within the bushing 18 to form a composite assembly, which is easily disassembled when die 10 is to be removed from the base 12. Ribs 16 form alignment means for the reinsertion of the die section 10 onto the cast base 12 and prevent the die from turning when the latter is remounted on the base.

Figure 3:
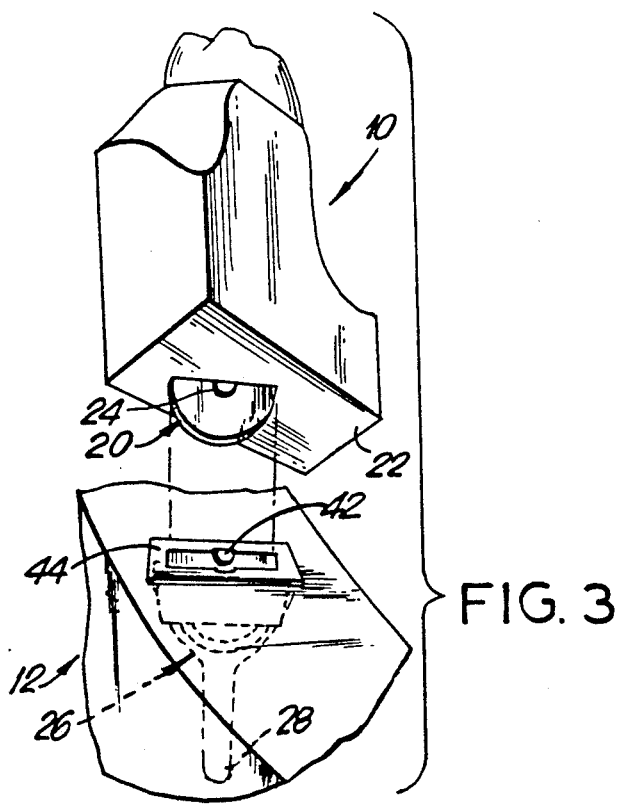
FIG. 3 is an exploded perspective view of the system for coupling the cast base and the model die according to the present invention.

Referring now to FIG. 3, it will be seen that the disc and sleeve arrangement according to the present invention includes a disc 20 inserted into the die segment 10 with a part of the disc projecting downwardly from a lower surface 22 of the die 10. Two knobs 24 are provided at opposing sides of the disc 20. The second part of the coupling arrangement is constituted by a sleeve 26 cast within the base 12 and which snugly receives the projecting portion of disc 20 as will be described in detail below.

Figure 4:
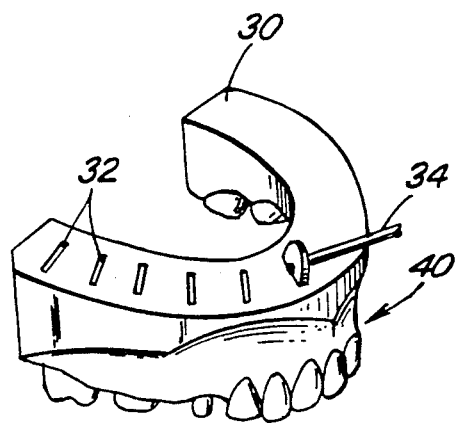
FIGS. 4 to 6 show the steps of making of the disc and sleeve system of the invention.
Figure 5:
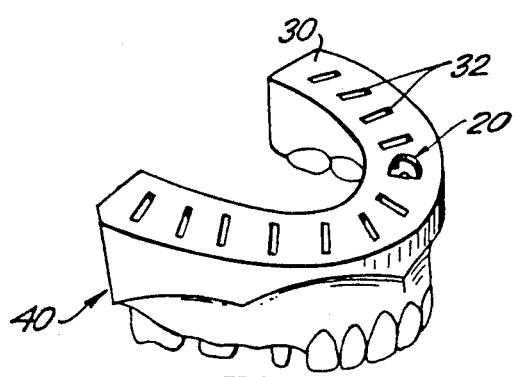
Figure 6:
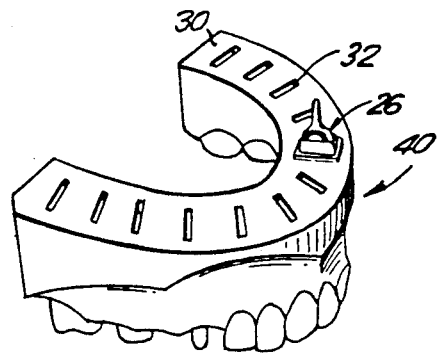

With reference to FIGS. 4 to 6 it will be seen that in order to facilitate manufacture of the dental model with the coupling system according to the invention, the underside surface 30 of a dental model 40 which will eventually be cut into a number of segments or dies 10 is formed with a plurality of cuts 32 circumferentially spaced apart from each other. Cuts 32 are substantially semi-circular in shape and are made by a tool designed for the task. Discs 20 are then inserted and secured into cuts 32 as shown in FIG. 5. Cuts 32 sawed in the ground plane of the model 40 are maintained vertical and parallel to each other. The number of the cuts is selected such that at least one cut is located in each part or die which would be removable in the model. The disc 2 is then secured in each cut 32 as illustrated in FIG. 5. Discs 20 may be fixed in cuts 32 by means of cement or any other adequate adhesive material. Cuts 32 are easy to make and their spacing can be easily selected depending on the segments or dies 10 to be removed from the model to be worked on. Additionally, only one cut per die segment is needed. The discs are formed such that only the semi-circular upper portions fit into the cuts. The bottom portions project from the bottom surface, as shown in FIG. 5. FIG. 6 then illustrates the sleeve 26 snapped on the projecting part of disc 20.

Figure 7:
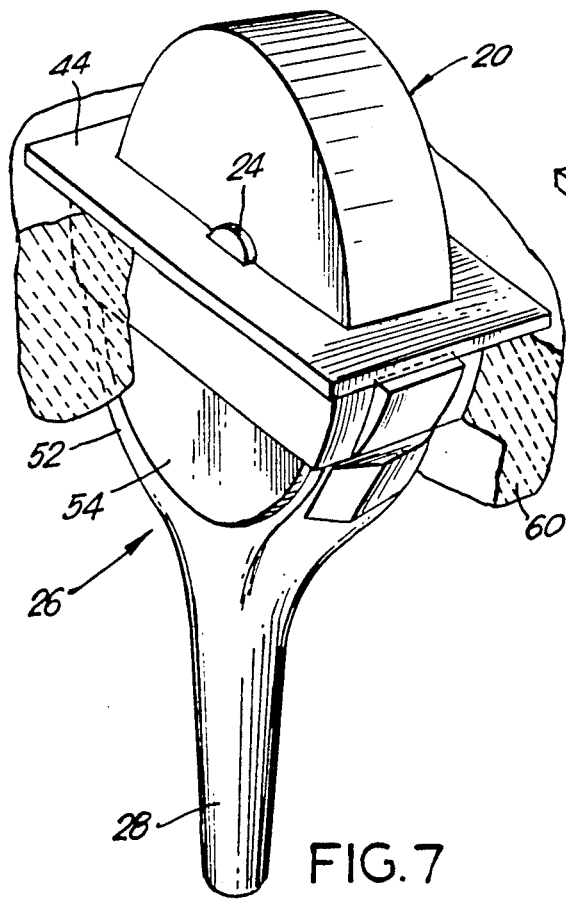
FIG. 7 is a perspective view of the disc and sleeve coupling assembly of the invention.
Figure 8:
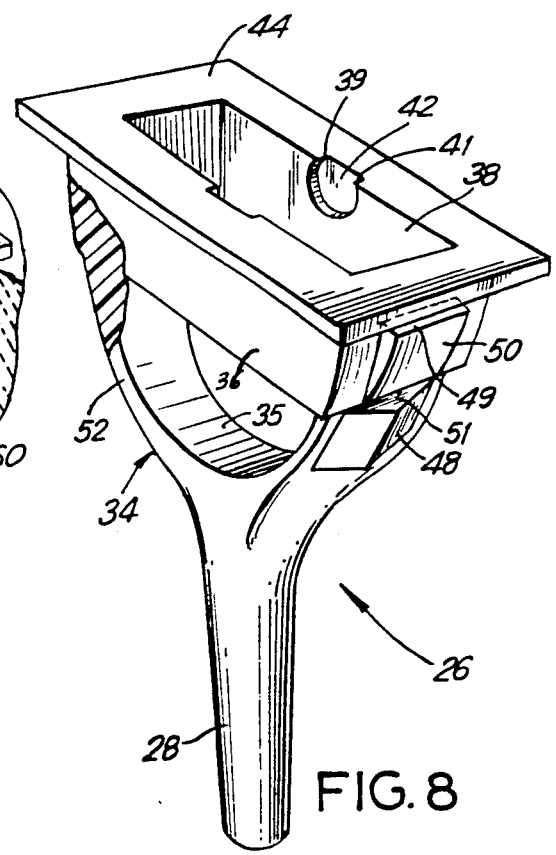
FIG. 8 is a perspective view of the sleeve with portions thereof cut away.

As best seen in FIGS. 7 and 8, sleeve 26 includes a substantially cylindrical elongated tail portion 28 which merges into a U-shaped head portion 34 having a concave inner surface 35 and terminated with a housing frame 36. Head portion 34 is formed with a semicircular chamber 38 interior of the frame 36 into which the portion of disc 20 protruding from the die 10 is received. Two semi-circular recesses 42 of a configuration mating that of the knobs 24 are provided at two longitudinal internal walls of the housing frame 36. Depressions 42 are slightly greater than a semicircle to that the arcuate tips 39,41 provide a reliable snap lock for knobs 24 when the protruding portion of disc 20 is received into the semi-circular chamber 38 of sleeve 26.

After sleeves 26 are snapped onto the discs 20, embedded in the dental model 40, as shown in FIG. 6, a stone material is poured onto the base of the model 4 with the disc and sleeve assemblies thereon to form a cast base portion which will support the model. The model will be later cut into segments or dies and each die will be capable of remounting onto the base with the aid of the disc and sleeve arrangements.

Housing frame 36 provided at the upper end of sleeve 26 is of a substantially rectangular configuration and has a stabilizing flat enlarged upper flange 44 which in assembly seats onto the cast base and forms part of the smooth planar surface of the cast base. This flange rests on the underside 30 of the cast 40. The flange assists in supporting the sleeve 26 in its vertical position when the stone material or plaster is poured over the model 40 to cast the base 60. The U-shaped head portion 3 and its flange 36 have externally protruding lugs 48 and 50, respectively provided at two opposite sides of the sleeve 26 and forming means to securely retain the sleeve within the stone material. Lugs 48, 50 are triangular in shape as shown in FIG. 8 thereby providing a flat upper surface 49, 51 to prevent upward loosening of the sleeve from the stone base. It is, of course, understandable that other shapes of the lugs could be used to ensure the material retention function thereof.

In assembly, interior chamber 38 snugly accommodates the portion of disc 20 protruding from the underside 30 of the model 40. The thickness of walls 52 of the U-shaped head portion 34 is selected so as to be sufficient to reliably hold the protruding portion 54 of disc 20 when the dies 10 of the model 40 are mounted on the cast base 60. At the same time they must be sufficiently flexible to permit extraction of this protruding portion from the head portion 34 of the sleeve 26 when a die segment 10 is removed from cast base 60. The depth of the interior chamber 38 is selected so that approximately three fifths of the disc 20 is inserted in the recess in the assembled position of the arrangement while two fifths of disc 20 is embedded in cast 40. Accordingly, as best seen in FIG. 7, the disc protruding portion 54 snugly fits within the sleeve 26 to form a composite assembly.

FIGS. 9 to 12 illustrate various modifications of the disc 20. As best seen in FIGS. 9A and 9B, disc 20 is of a substantially circular configuration and has two cylindrical knobs 24 formed, preferably by casting, at two diametrically opposing sides of the disc for a snap fit into two correspondingly diametrically opposing depressions 42 of sleeve 26, as has been described above.

Figures 9A, 9B, 10A, 10B:
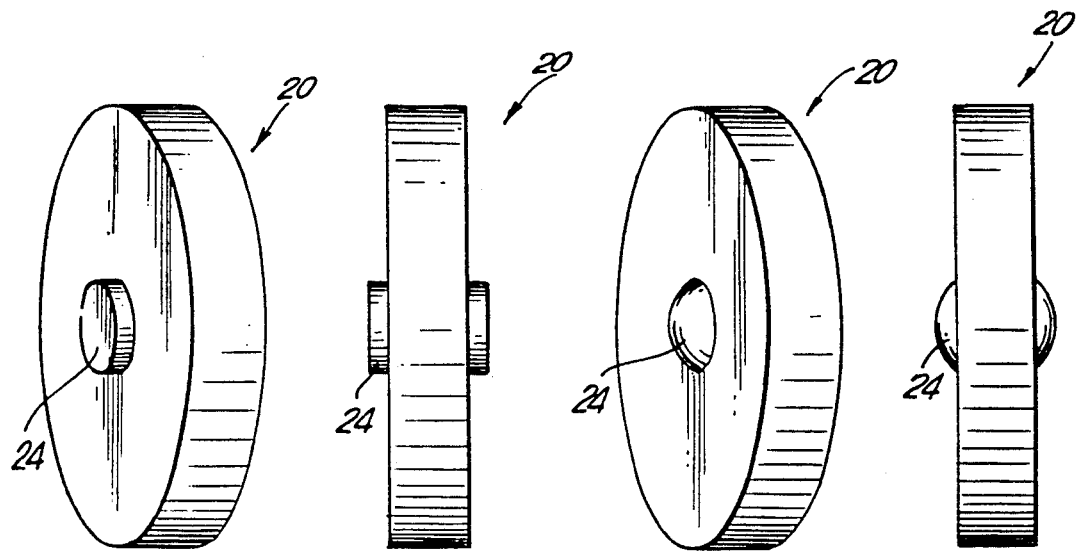

The embodiment of FIGS. 10A and 10B differs from that of FIGS. 9A and 9B in that knobs 24 ar substantially semi-spherical. It is apparent that depressions 42 in the sleeve 26 for accommodating such knobs would also be of semi-spherical configuration mating that of knobs 24.

Figures 11A, 11B:
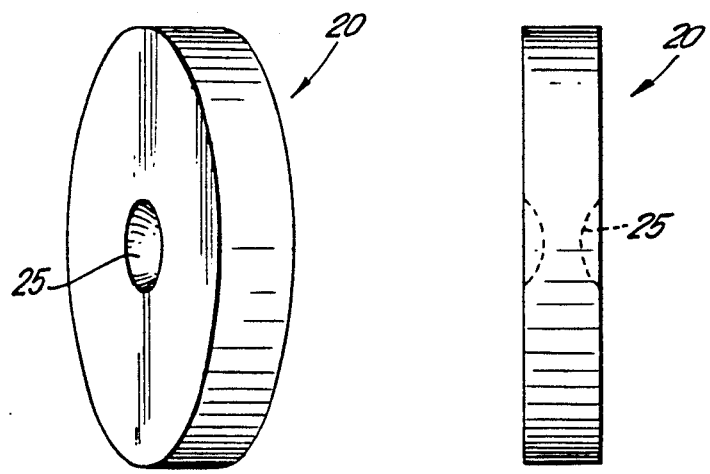

FIGS. 11A and 11B depict yet another variant of the disc structure. Semi-spherical grooves 25 are formed at two diametrically opposing sides of the circular disc 20, which grooves in the assembled state of disc 20 with the sleeve 26 will receive corresponding semi-spherically shaped projections provided at two opposite internal faces of the frame 38 of head portion 34 of sleeve 26 The semi-spherical projections on the sleeve would snap into the grooves on the disc to provide a snug fit of the disc within the sleeve to form a composite assembly when any die segment is remounted on the cast base 60.

Figures 12A, 12B, 12C, 12D:
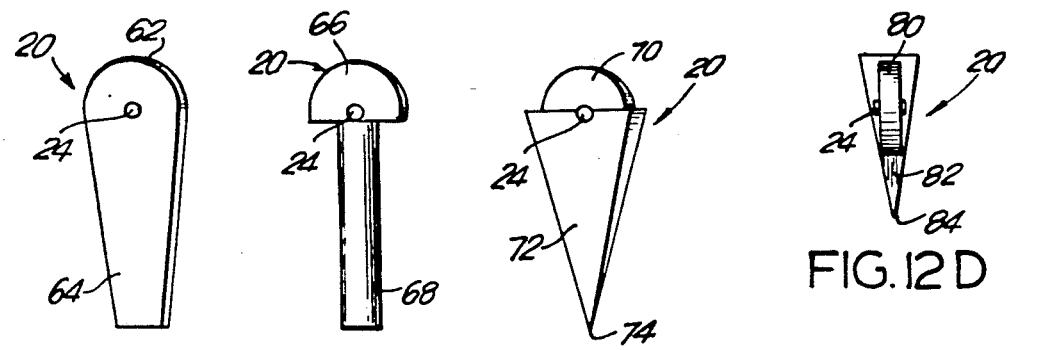

FIG. 12A shows yet another variation of the disc 20 inserted in the hole 32 of the model 40 and adapted to snugly fit in a corresponding sleeve embedded in the cast base 60. Disc 20 in this embodiment is an elongated, substantially flat element, the upper portion 62 of which again has a semi-circular cross-section to fit in the same semi-circular saw cut 32 previously described. However, instead of a semi-circular lower portion which would project from the bottom of the model there is now provided a lower elongated portion 64 which tapers downwardly. This elongated tapering portion 64 would be accommodated in a correspondingly shaped recess in a sleeve to be snugly fit therein in the assembled condition and permits easy pulling of elongated portion 64 from the sleeve to remove a respective die segment from the cast base 60. The projecting knobs 24 would still be used to snap fit the disc into the sleeve.

FIG. 12B illustrates a disc element 20 which again includes a disc-shaped upper portion 66 insertable in the semi-circular saw cut 32 (FIG. 4) and now includes an elongated protruding rod-like portion 68 joined with the disc-shaped portion 66 and being of the same thickness therewith. The two knobs 24 are provided for fitting in respective depressions of sleeve 26 for snap fitting the disc into the sleeve. The sleeve would include a chamber to receive the rod-like projection.

In the embodiment of FIG. 12C, the internal element 20 of the disc-and-sleeve assembly again includes the disc-shaped portion 70 insertable into the semi-circular saw cut 32 of the model 40, and now includes an elongated portion 72 of a substantially pyramidal configuration sloping towards a distal end 74 which forms an apex of the pyramid. Knobs 24 are formed at the upper edge of elongated portion 72 in the manner similar to that of the aforedescribed embodiments.

FIG. 12D depicts a top plan view of another disc element 20 which includes a disc-shaped portion 80 and a substantially triangular portion 82 which would extend downwardly from the disc in a manner similar to that of FIGS. 12A-12C. The cross-sectional triangular shape has one end 84 pointed. Two knobs 24 of a substantially cylindrical shape are formed at two opposite sides of disc-shaped portion 80. Disc-shaped portion 80 would be inserted in saw cut 32 while the triangular piece or portion 82 would be accommodated in a corresponding recess of the sleeve.

Figure 12E:
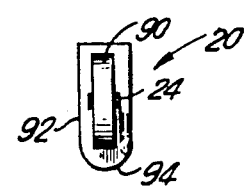

FIG. 12E shows a top plan view of a still another version of the internal disc element 20. The element 20 again includes a disc-shaped portion 90 and an elongated element projecting therefrom in a manner similar to FIGS. 12A-12C. The projection portion has a cross-sectional configuration shown at 92 which is a substantially rectangular configuration with one end 94 being curved. The top of portion 92 forms a flange below the disc which is received in a recess of the corresponding sleeve of the assembly. Knobs 24 could snap fit in two opposing grooves of the sleeve.

In all the embodiments of the internal or male element of the snap-in assembly of the invention, the disc-shaped portion of each element ensures its easy insertion in the respective semicircular saw cut 32 of the dental model while the protruding portion of this internal element is received in the base. The protruding portion may be the remaining part of a circular disc or a vertically extending rod like portion. The combination of the disc and sleeve ensures a reliable seating of the segment into the base and permits easy removability of the segments. Nevertheless in each case only a single cut is required in each die segment and into which the semicircular disc is inserted. This provides orientation for returning the segment. Also, the presence of the knobs provide good lock means for locking of the disc in the sleeve. In all exemplified embodiments, the portion of the internal member 20 received and secured in the saw cut 32 has a semi-circular configuration mating that of each saw cut 32 formed in the underside of model 40.

It should be noted that in the embodiment of FIGS. 9A to 11B disc 20 may be inserted into sleeve 26 in two 180° opposite positions. On the other hand, the vertically extending portions of the embodiments of FIGS. 12A-12E constitute orientation means which ensure the insertion of the internal disc elements 20 into the sleeve 26 in a single insertion position. In all the embodiments, however, a reliable snap lock of the disc and sleeve assembly is provided to connect the die segment to the said base and an easy disassembling of these two parts to remove the die segment from the cast base.

It should be emphasized that in all the embodiments only a single hole and a single snap-in assembly of the invention are necessary for each die segment to be removed from and remounted on the cast base whereas in other prior art systems at least two holes and two pins are necessary for a proper orientation and removable connection of a die segment to the cast base. Furthermore, the continuous reinsertion of the cylindrical pins into the sleeves may cause the assembly to become loose and shaky. These disadvantages are eliminated with the snap-fit disc-and-sleeve assembly according to the invention. Only a single sawing operation is required to produce semi-circular cut 32 in the underside of the dental model according to the present invention and the snap fit ensures a tight fit.

Figure 13:
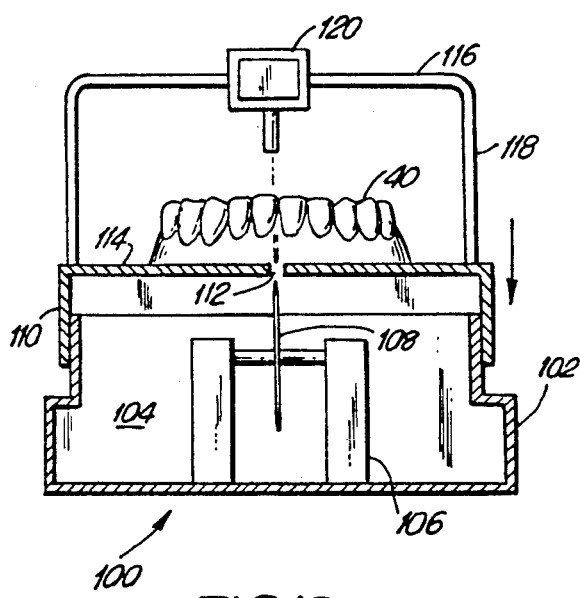
FIG. 13 is a front view, partially in section, of a device for sawing a semi-circular cuts into the lower surface of the model.

FIG. 13 schematically illustrates a rotary saw assembly which can be used for making the saw cuts into the underside of the model 40. The rotary saw of FIG. 13 designated at 100 includes a housing 102 which defines a housing compartment 104 in which a motor-driven rotary saw 106 is accommodated. A vertically movable work table 110 supports thereon the cast model 40 onto which the saw cuts are to be made A slit 112 is provided in a supporting plate 114 of the work table 110 so that the cutter or saw blade 108 can extend upwardly through the slit as the work table descends. In the normal, uppermost position, as shown in solid line in FIG. 13, the blade is completely recessed beneath the work table and directly under the slit 112 in the supporting plate 114. As the work table is lowered by depression of the model onto the supporting plate 114 the blade becomes exposed as it emerges upwardly through the slit above the top surface of plate 114, as shown in dotted line in FIG. 13, and the saw cut into the underside of model 40 is performed. Depending from a transverse arm 116 of an upper part 118 of the work table rigidly connected to the supporting plate 114, is a beam light 120 which is focused so that it is directly over a section of the die to be segmented and identifies the cutting point at the diametric top of the rotary blade. Model 40 may then be shifted horizontally to position the model such that a next portion to be segmented is oriented over the saw blade.

Figure 14:
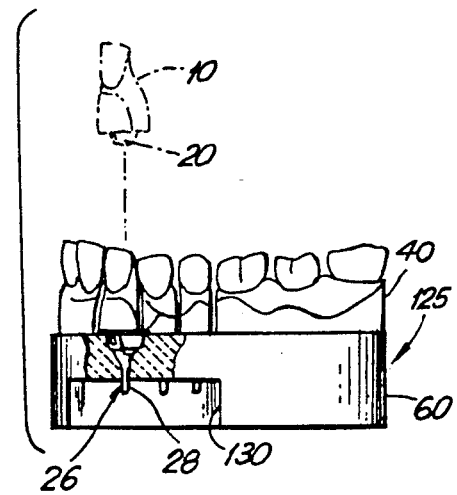
FIG. 14 shows the removal and re-insertion of a die section into the model, using the disc-and-sleeve assembly according to the invention.

FIG. 14 illustrates a working cast 125 which includes base 60 and model 40 mounted thereon.

As seen in FIG. 14 the die 10 (shown in dotted line) carrying the single disc 20 therein can be remounted onto the cast base 60 whereby the disc 20 snap-fits in the sleeve 26 assigned thereto. In this manner an initial position of die segment 10 relative to the base and relative to the orientation of the protruding disc-portion of disc 20 in the sleeve 26. Due to knobs 24 received in the respective depressions of the sleeve 26 the die section 10 will fit snugly on the base 60 as the die section is pushed into place. As also shown in FIG. 14 the cylindrical tail 28 of the sleeve 26 projects into a notch 130 cut onto the underside of base 60 of the working cast 125. Pushing up on the distal end of tail 28 of the sleeve would spread the arms on each side of the head portion 36 of the sleeve to facilitate release of disc 20 from the sleeve and thus the removal of die segment 10 from the base 60. The disc and the sleeve may be made of plastic or metal material as is well known in this field.

There has been disclosed heretofore the best embodiment of the invention presently contemplated. However, it is to be understood that various changes and modifications may be made thereto without departing from the spirit of the invention.

I claim:

1. A dental pin and sleeve assembly for removably-coupling a die section of a dental model into a cast base, the assembly comprising:

a pin member including an internal portion for securement within said die section and an exterior portion protruding from said die section to depend therefrom, said internal portion being of a substantially semi-circular configuration; and a sleeve member for securement within said cast base, said sleeve member including a head portion having a chamber which is opened at an upper face of said cast base to wholly receive said exterior protruding portion when said die section is coupled to said cast base.

2. A dental pin and sleeve assembly as in claim 1, wherein said exterior portion and said head portion include cooperate lock means for providing a releasable snap-fit lock of said exterior portion into said head portion when said die section is coupled into said cast base.

3. A dental pin and sleeve assembly as in claim 2, wherein said lock means include two knobs positioned at two opposite sides of said exterior protruding portion and two correspondingly shaped depressions formed in said sleeve member and receiving said two knobs, respectively.

4. A dental pin and sleeve assembly as in claim 2, wherein said head portion is substantially semi-circular in shape and is provided with a chamber shaped to matingly receive said exterior protruding portion.

5. A dental pin and sleeve assembly as in claim 4, wherein said lock means on said exterior protruding portion includes two knobs provided at two opposite sides thereof.

6. A dental pin and sleeve assembly as in claim 5, wherein said lock means on said head portion includes two grooves formed at two opposite walls of said chamber and receiving said knobs to provide said snap-fit lock.

7. A dental pin and sleeve assembly as in claim 6, wherein said head portion includes a hollow frame formed with said grooves and having an interior shaped chamber to matingly receive said protruding exterior portion.

8. A dental pin and sleeve assembly as in claim 7, wherein said frame has an external surface formed with lugs protruding from said surface to retain said sleeve within said cast base.

9. A dental pin and sleeve assembly as in claim 7, wherein said head portion is formed with outwardly protruding lugs positioned at two opposite sides thereof to retain said sleeve within said cast base.

10. A dental pin and sleeve assembly as in claim 7, wherein said knobs are substantially disc-shaped.

11. A dental pin and sleeve assembly as in claim 7, wherein said knobs are substantially semi-spherical.

12. A dental pin and sleeve assembly as in claim 6, wherein said lock means on said exterior protruding portion includes two grooves provided at two opposite sides of said disc.

13. A dental pin and sleeve assembly as in claim 12, wherein said lock means on said head portion includes two knobs provided at two opposite walls limiting said chamber and being snapped in said grooves to provide said snap-fit lock.

14. A dental pin and sleeve assembly as in claim 1, wherein said sleeve member comprises a substantially cylindrical tail portion depending from said head portion.

15. A dental pin and sleeve assembly as in claim 1, wherein said exterior portion is of a substantially semicircular configuration and constitutes with said internal semicircular portion a complete disc.

16. A dental pin and sleeve assembly as in claim 15, wherein said head portion has a substantially U-shaped chamber for matingly received said exterior protruding portion.

17. A dental pin and sleeve assembly as in claim 1, wherein said head portion is a frame which has an internal chamber for matingly receiving said exterior protruding portion.

18. A dental pin and sleeve assembly as in claim 1, wherein said pin member is a complete disc.

19. A dental pin and sleeve assembly as in claim 1, wherein said head portion includes retention means on an external surface thereof, said means aiding in the retention of said sleeve within the cast base.

20. A dental pin and sleeve assembly as in claim 1, wherein said exterior protruding portion is elongated and tapers in a direction away from said internal portion to orient said exterior protruding portion upon insertion thereof into said chamber of said sleeve member.

21. A dental pin and sleeve assembly as in claim 1, wherein said exterior protruding portion is an elongated rod of a thickness corresponding to that of said internal portion and adapted to orient said exterior protruding portion upon insertion thereof into said chamber of said sleeve member.

22. A dental pin and sleeve assembly as in claim 1, wherein said exterior protruding portion is elongated and of a substantially pyramidal shape with an apex facing away from said internal portion to orient said exterior protruding portion upon insertion thereof into said chamber of said sleeve member.

23. A dental pin and sleeve assembly as in claim 1, wherein said exterior protruding portion includes an elongated portion having a substantially triangular cross sectional configuration.

24. A dental pin and sleeve assembly as in claim 1, wherein said exterior protruding portion includes an elongated section having a substantially rectangular cross sectional configuration with one edge rounded.

25. A dental pin and sleeve assembly for removably-coupling a die segment of a dental model to a cast base, said die segment being removable and remountable onto said base, the assembly comprising:

a disc-shaped element partially inserted in and secured within said die segment so that a portion of said element depends from and extends normal to an underside of said die segment; and a sleeve secured within said base and receiving said portion of said disc-shaped element, said sleeve including a head portion having a recess which is opened at an upper side of said base and shaped to matingly receive said portion of said disc-shaped element.

26. A dental pin and sleeve assembly as in claim 25, wherein said disc-shaped element and said recess are provided with connecting lock means to ensure a releasable snap-fit lock of said portion of said disc-shaped element in said head portion when said die segment is mounted on said cast base.

27. A dental pin and sleeve assembly as in claim 26, wherein said lock means include two knobs positioned at two opposite sides of one of said disc-shaped element and sleeve, and two grooves formed at two opposite sides of other of said disc-shaped element and sleeve for receiving said knobs.

28. A method of making a model of teeth wherein die portions of the model may be removed and remounted from a base, the method comprising the steps of cutting a plurality of substantially semi-circular cuts in an underside of the model opposite to that formed with the teeth, fixing a disc-shaped element in each cut so that a portion of said element extends normal to and outwardly from said underside of the model, mounting on outwardly extending portions of disc-shaped elements sleeves each having a recess matingly receiving said portion of a respective disc-shaped element, pouring a cast material over said model with said disc-shaped elements and said sleeves thereon to form the base, allowing said material to harden for securing each sleeve in said base, removing said model together with said elements from said hardened base, and cutting said model into die portions so that each die portion includes at least one disc-shaped element protruding therefrom, said die portions being remountable on said base by insertion of said portion of each disc-shaped element into said recess of a respective sleeve.

29. A dental pin and sleeve assembly for removably-coupling a die section of a dental model into a cast base, the assembly comprising:

a pin member including an internal portion for securement within said die section and an exterior portion protruding from said die section to depend therefrom, said internal portion being of a substantially semi-circular configuration; and a sleeve member for securement within said cast base including a head portion having a chamber for receiving said protruding portion when said die section is coupled to said base, wherein said exterior portion and said head portion include cooperating lock means for providing a releasable snap-fit lock of said exterior portion into said head portion when said die section is coupled into said cast base.

30. A dental pin and assembly for removably-coupling a die section of a dental model into a cast base, the assembly comprising:

a pin member including an internal portion for securement within said die section and an exterior portion protruding from said die section to depend therefrom, said internal portion being of a substantially semi-circular configuration; and a sleeve member for securement within said cast base including a head portion having a chamber for receiving said protruding portion when said die section is coupled to said base, said sleeve member comprising a substantially cylindrical tail portion depending from said head portion.

31. A dental pin and sleeve assembly for removably-coupling a die section of a dental model into a cast base, the assembly comprising:

a pin member including an internal portion for securement within said die section and an exterior portion protruding from said die section to depend therefrom, said internal portion being of a substantially semi-circular configuration; and a sleeve member for securement within said cast base including a head portion having a chamber for receiving said protruding portion when said die section is coupled to said base, wherein said exterior portion is of substantially semi-circular configuration and constitutes with said internal semi-circular portion a complete disc, said head portion having a substantially U-shaped chamber for matingly receiving said exterior portion.

32. A dental pin and sleeve assembly for removably-coupling a die section of a dental model into a cast base, the assembly comprising:

a pin member including an internal portion for securement within said die section and an exterior portion protruding from said die section to depend therefrom, said internal portion being of a substantially semi-circular configuration; and a sleeve member for securement within said cast base including a head portion having a chamber for receiving said protruding portion when said die section is coupled to said base, wherein said exterior portion and said head portion include cooperating lock means for providing a releasable snap-fit lock of said exterior portion into said head base, said lock means including two knobs positioned at two opposite sides of said exterior protruding portion and two correspondingly shaped depressions formed in said sleeve member and receiving said two knobs, respectively.

33. A dental pin and sleeve assembly for removably-coupling a die section of a dental model into a cast base, the assembly comprising:

a pin member including an internal portion for securement within said die section and an exterior portion protruding from said die section to depend therefrom, said internal portion being of a substantially semi-circular configuration; and a sleeve member for securement within said cast base including a head portion having a chamber for receiving said protruding portion when said die section is coupled to said base, wherein said pin member is a complete disc and said head portion is substantially semi-circular in shape and is provided with a chamber shaped to matingly receive said exterior portion.

34. A dental pin and sleeve assembly for removably-coupling a die section of a dental model into a cast base, the assembly comprising:

a pin member including an internal portion for securement within said die section and an exterior portion protruding from said die section to depend therefrom, said internal portion being of a substantially semi-circular configuration; and a sleeve member for securement within said cast base including a head portion having a chamber for receiving said protruding portion when said die section is coupled to said base, said exterior portion and said head portion including cooperating lock means for providing a releasable snap-fit lock of said exterior portion into said head portion when said die section is coupled into said cast base, said pin member being a complete disc, said head portion being substantially semi-circular in shape and is provided with a chamber shaped to matingly receive said exterior portion, wherein said lock means on said exterior portion includes two knobs provided at two opposite sides thereof.

35. A dental pin and sleeve assembly as in claim 34, wherein said lock means on said head portion includes two grooves formed at two opposite walls of said chamber and receiving said knobs to provide said snap-fit lock.

36. A dental pin and sleeve assembly as in claim 35, wherein said head portion includes a hollow frame formed with said grooves and having an interior shaped chamber to matingly receive said protruding exterior portion.

37. A dental pin and sleeve assembly as in claim 36, wherein said frame has an external surface formed with lugs protruding from said surface to retain said sleeve within said cast base.

38. A dental pin and sleeve assembly as in claim 36, wherein said head portion is formed with outwardly protruding lugs positioned at two opposite sides thereof to retain said sleeve within said cast base.

39. A dental pin and sleeve assembly as in claim 36, wherein said knobs are substantially disc-shaped.

40. A dental pin and sleeve assembly as in claim 36, wherein said knobs are substantially semi-spherical.

41. A dental pin and sleeve assembly as in claim 35, wherein said lock means on said exterior portion includes two grooves provided at two opposite sides of said disc.

42. A dental pin and sleeve assembly for removably-coupling a die section of a dental model into a cast base, the assembly comprising:

a pin member including an internal portion for securement within said die section and an exterior portion protruding from said die section to depend therefrom, said internal portion being of a substantially semi-circular configuration; and a sleeve member for securement within said cast base including a head portion having a chamber for receiving said protruding portion when said die section is coupled to said base, wherein said exterior protruding portion includes an elongated section having a substantially rectangular cross-section configuration with one edge rounded, said chamber being of such depth that it receives said exterior portruding portion over a length thereof greater than that of said internal portion for securement within said die section.

43. A dental pin and sleeve assembly for removably-coupling a die section of a dental model into a cast base, the assembly comprising:

a pin member including an internal portion for securement within said die section and an exterior portion protruding from said die section to depend therefrom, said internal portion being of a substantially semi-circular configuration; and a sleeve member for securement within said cast base including a head portion having a chamber for receiving said protruding portion when said die section is coupled to said base, wherein said disc-shaped element and said chamber are provided with connecting lock means to ensure a releasable snap-fit lock of said portion of said disc-shaped element in said head portion when said die segment is mounted on said cast base.

44. A dental pin and sleeve assembly as in claim 43, wherein said lock means include two knobs positioned at two opposite sides of one of said disc-shaped element and sleeve, and two grooves formed at two opposite sides of other of said disc-shaped element and sleeve for receiving said knobs.

* * * * *